(12) United States Patent
Farnum

(10) Patent No.: US 10,034,820 B2
(45) Date of Patent: Jul. 31, 2018

(54) PERSONAL CARE FORMULATION AND USES THEREOF

(71) Applicant: BRYSON PATENTS INC., King City (CA)

(72) Inventor: Bryan Christopher Farnum, King City (CA)

(73) Assignee: BRYSON PATENTS INC., King (CA)

( * ) Notice: Subject to any disclaimer, the term of this patent is extended or adjusted under 35 U.S.C. 154(b) by 0 days.

(21) Appl. No.: 14/912,616

(22) PCT Filed: Aug. 27, 2014

(86) PCT No.: PCT/CA2014/000657
§ 371 (c)(1),
(2) Date: Feb. 18, 2016

(87) PCT Pub. No.: WO2015/027323
PCT Pub. Date: Mar. 5, 2015

(65) Prior Publication Data
US 2016/0199292 A1      Jul. 14, 2016

Related U.S. Application Data

(60) Provisional application No. 61/870,559, filed on Aug. 27, 2013.

(51) Int. Cl.
| | |
|---|---|
| *A61Q 11/00* | (2006.01) |
| *A61K 8/92* | (2006.01) |
| *A61K 8/19* | (2006.01) |
| *A61K 8/25* | (2006.01) |
| *A61K 8/34* | (2006.01) |
| *A61K 8/365* | (2006.01) |
| *A61K 8/73* | (2006.01) |
| *A61K 8/97* | (2017.01) |
| *A61Q 1/14* | (2006.01) |
| *A61Q 19/00* | (2006.01) |
| *A61Q 19/08* | (2006.01) |
| *A61Q 19/10* | (2006.01) |

(52) U.S. Cl.
CPC ............ *A61K 8/19* (2013.01); *A61K 8/25* (2013.01); *A61K 8/345* (2013.01); *A61K 8/365* (2013.01); *A61K 8/73* (2013.01); *A61K 8/731* (2013.01); *A61K 8/922* (2013.01); *A61K 8/97* (2013.01); *A61Q 11/00* (2013.01); *A61Q 19/00* (2013.01); *A61Q 19/001* (2013.01); *A61Q 19/007* (2013.01); *A61Q 19/10* (2013.01); *A61K 2800/28* (2013.01); *A61K 2800/30* (2013.01); *A61K 2800/48* (2013.01); *A61K 2800/5922* (2013.01); *A61Q 1/14* (2013.01); *A61Q 19/08* (2013.01)

(58) Field of Classification Search
CPC .......... A61Q 11/00; A61K 8/922; A61K 8/19; A61K 8/25; A61K 8/97; A61K 8/731; A61K 19/10; A61K 19/0007; A61K 19/08; A61K 8/92; A61K 8/345; A61K 8/73

See application file for complete search history.

(56) References Cited

U.S. PATENT DOCUMENTS

| | | | | |
|---|---|---|---|---|
| 2008/0031831 | A1* | 2/2008 | Laali | A61K 8/922 424/58 |
| 2010/0008869 | A1* | 1/2010 | Takagi | A61K 8/042 424/55 |
| 2012/0225022 | A1* | 9/2012 | Hier | A61K 8/97 424/9.71 |

FOREIGN PATENT DOCUMENTS

WO   WO 20013/098413      * 7/2013

OTHER PUBLICATIONS

Organic Natural Health Website, Natural Skin Care Products Garnet Exfoliant, retrieved from the internet: http://web.archive.org/web/20120422024711/http://www.health-report.co.uk/ingredients.htm; [retrieved on Dec. 1, 2014].
Survana Website, Organic Aloe Exfoliating Cream, retrieved from the internet: http://web.archive.org/web/20120531172812/http://www.suvarna.co.uk/exfoliants/sensitivefacialscrub.html; [retrieved on Dec. 1, 2014].
Riddells Creek Website, Organic Toothpaste 100g—Lemon, retrieved from the internet: http://web.archive.org/web/20130307052202/http://www.riddellscreekorganic.com.au/store/oral-care/organic-toothpaste-100g-lemon-aco-95-detail; [retrieved on Dec. 1, 2014].
International Search Report of PCT/CA2014/000657; Gatineau; dated Dec. 15, 2014; Savard, Catherine.

* cited by examiner

*Primary Examiner* — Lezah Roberts
(74) *Attorney, Agent, or Firm* — Benoit & Cote Inc.; Mathieu Miron

(57) ABSTRACT

The present document describes a personal care formulation comprising from about 2% to about 50% (vol/vol) of at least one edible oil; from about 0.02% to about 0.08% (wt/vol) of at least one edible abrasive; and a thickening agent mixture comprising from about 3% to about 66% (vol/vol) of at least one first thickening agent chosen from aloe vera gel, aloe vera juice, xanthan gum, and cellulose gum, or from about 0.1% to about 0.3% (wt/vol) of carrageenan, or combinations thereof. The present document also describes use of the formulation of skin care and oral hygiene.

13 Claims, No Drawings

PERSONAL CARE FORMULATION AND USES THEREOF

CROSS-REFERENCE TO RELATED APPLICATIONS

This application is a US National Phase application under 35 USC § 371 of PCT/CA2014/000657, filed Aug. 27, 2014, which in turn, claims priority and the benefit of U.S. provisional patent application 61/870,559 filed Aug. 27, 2013. Applicant claims the benefits of 35 U.S.C. '120 as to the PCT application and priority under 35 U.S.C. '119 as to the said U.S. Provisional patent application, and the entire disclosures of both applications are incorporated herein by reference in their entireties.

BACKGROUND (a) Field

The subject matter disclosed generally relates to a personal care composition, and more specifically to personal care compositions containing oils, tinctures, abrasive, and thickening agent.

(b) Related Prior Art

Synthetic as well as natural agents have been used for cleansing purposes. Soaps, surfactants and synthetic detergents have been used for decades for mouth, skin and hair cleansing. The objective of cleansing is to remove surface dirt, makeup, the top layer of dead skin cells, tartar, food particles, and potentially harmful microorganisms from the skin or oral cavity.

Soaps are made by reacting oils with alkali and are very efficient in removing dirt by emulsification. Unfortunately, there are problems with soaps: drying; and irritation of the skin due to excessive cleansing action and increased pH of the skin, and they are generally unsuitable cleansers for the mouth. Surfactants are typically synthetic compounds or materials which are good emulsifiers, but may be harsh to the skin and mucosa of the mouth. Synthetic detergents generally offer a better choice because their pH may be adjusted to that of skin or oral mucosa, but again they may dry the skin too much and cause irritation to the skin or oral mucosa. Both soap and the surfactants may be irritating to the eyes and may cause allergic reactions in some people. In addition formulations containing soap or surfactants typically provide little or no exfoliating or moisturizing effect, thus requiring the use of a separate exfoliant formulation and a moisturizing lotion or cream.

Thus, there is a need for stable personal care formulations containing no soap or a synthetic surfactant, providing simultaneous exfoliant, cleansing and moisturizing actions.

SUMMARY

According to an embodiment, there is provided a personal care formulation comprising:
from about 2% to about 50% (vol/vol) of at least one edible oil;
from about 0.02% to about 0.08% (wt/vol) of at least one edible abrasive; and
a thickening agent mixture comprising
from about 3% to about 66% (vol/vol) of at least one first thickening agent chosen from aloe vera gel, aloe vera juice, xanthan gum, and cellulose gum, or
from about 0.1% to about 0.3% (wt/vol) of carrageenan, or combinations thereof.

The personal care formulation of claim 1, wherein said at least one edible oil may be at least of orange oil, lemon oil, coconut oil, borage oil, pumpkin seed oil, or combinations thereof.

The at least one edible oil may be orange oil.

The orange oil may be from about 5% to about 15% (vol/vol) of the composition.

The at least one edible abrasive may be colloidal calcium, colloidal silica or both.

The at least one edible abrasive may be at least one of aluminum hydroxide $[Al(OH)_3]$, calcium carbonate $(CaCO_3)$, a calcium hydrogen phosphate, a hydrated silica, diatomaceous earth, a zeolite, a hydroxyapatite $(Ca_5(PO_4)_3OH)$, or combinations thereof.

The edible abrasive may be from about 0.1% to about 0.325% (wt/vol) of the composition.

The personal care formulation of claim 1 may further comprise from about 3% to about 20% (vol/vol) of at least one tincture.

The tincture may be dulse seaweed extract tincture, papaya leaf extract tincture, or combinations thereof.

The personal care formulation may further comprise a humectant.

The humectant may be propylene glycol, hexylene glycol, butylene glycol, glyceryl triacetate, vinyl alcohol, neoagarobiose, a sugar polyol, a polymeric polyol, quillaia, lactic acid, urea, glycerin, aloe vera gel, 2-Methyl-1,3-propanediol (MP diol), an alpha hydroxy acid, and honey The sugar polyol may be one or more of glycerol, sorbitol, xylitol and maltitol.

The polymeric polyol may be polydextrose.

The alpha hydroxyl acid may be sodium lactate, lactic acid, tartaric acid, malic acid, glycolic acid, glucose, citric acid, and combinations thereof.

The humectant may be from about 2% to about 5% (vol/vol) of the composition.

The personal care formulation may further comprise an emulsifier.

The emulsifier may be a lecithin, a vegetal pulp powder, and citric acid.

The vegetal pulp powder may be a citrus pulp powder, a baobab pulp powder, a mango pulp powder, a tomato pulp powder, a pumpkin pulp powder, a guava pulp powder, a papaya pulp powder and a beet pulp powder, or combinations thereof.

The emulsifier may be citric acid.

The emulsifier may be from about 4% to about 10% (wt/vol) of the formulation.

The personal care formulation may be substantially fluoride free.

According to another embodiment, there is provided a use of the personal care formulation of the present invention for the treatment of a skin.

The treatment of skin may comprise skin exfoliation, make-up removal, sun screening and blocking, and healing of damaged skin.

According to another embodiment, there is provided a personal care formulation of the present invention for use for oral hygiene.

The personal care formulation may be for teeth cleansing, teeth whitening, removal of dental tartar.

According to another embodiment, there is provided a method for skin care comprising topically applying the personal care formulation of the present invention to a skin.

The skin care may comprise skin exfoliation, make-up removal, sun screening and blocking, and healing of damaged skin.

According to another embodiment, there is provided a method of cleaning an oral cavity comprising applying the personal care formulation according to the present invention to an oral cavity.

The cleaning of an oral cavity may be for teeth cleansing, teeth whitening, removal of dental tartar.

The following terms are defined below.

The term "oral hygiene" is intended to mean the practice of keeping the mouth and teeth clean to prevent dental problems, most commonly, dental cavities, gingivitis, and bad breath. It is also intended to mean the good oral hygiene required for healing and regeneration of the oral tissues affected by pathologic conditions. These conditions included gingivitis, periodontitis, and dental trauma, such as subluxation, oral cysts, and following wisdom tooth extraction.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

DETAILED DESCRIPTION

In embodiments there is disclosed a personal care formulation which comprises:
  from about 2% to about 50% (vol/vol) of at least one edible oil;
  from about 0.02% to about 0.08% (wt/vol) of at least one edible abrasive; and
  a thickening agent mixture comprising
    from about 3% to about 66% (vol/vol) of at least one first thickening agent chosen from aloe vera gel, aloe vera juice, xanthan gum, and cellulose gum, or
    from about 0.1% to about 0.3% (wt/vol) of carrageenan, or combinations thereof.

In another embodiment there is disclosed a personal care formulation which comprises:
  from about 2% to about 50% (vol/vol) of at least one oil chosen from orange oil, lemon oil, coconut oil, or borage oil;
  from about 3% to about 20% (vol/vol) of at least one tincture chosen from dulse seaweed extract tincture or papaya leaf extract tincture;
  from about 0.100% to about 0.325% (wt/vol) of at least one abrasive chosen from colloidal calcium or colloidal silica; and
  a thickening agent mixture comprising
    from about 3% to about 66% (vol/vol) of at least one first thickening agent chosen from aloe vera gel, aloe vera juice, xanthan gum, and cellulose gum, and/or
    from about 0.1% to about 0.3% (wt/vol) of carrageenan.

The personal care formulation of the present invention may be used for a wide range of personal body care functions, such as teeth cleansing (including teeth brushing, teeth whitening and tartar removal), skin exfoliation, make-up removal, sun screening and blocking, healing of damaged skin, such as scratches, and skin burns, and promoting general wellness when ingested orally by an individual.

The personal care formulation of the present invention contains a number of components, which are described in further details below.

Edible Oils

According to an embodiment, the personal care formulation of the present invention contains at least one oil chosen from orange oil, lemon oil, coconut oil, borage oil or pumpkin seed oil.

Orange oil is an essential oil produced by cells within the rind of an orange fruit. It is composed of mostly (greater than 90%) d-limonene, and is often used in place of pure d-limonene. D-limonene can be extracted from the oil by distillation. Limonene gives citrus fruit their familiar aroma, and is therefore used in perfume and household cleaners for its fragrance. It is also an effective, environmentally friendly, and relatively safe solvent, which makes it an active ingredient of choice in many applications, such as, but not limited to, adhesive and stain removers, cleaners of various sorts, and strippers. It is very useful in agriculture. Orange oil has also been shown to display useful antiseptic and antimicrobial properties, as well as anti-inflammatory and detoxifying properties. In the compositions of the present invention, orange oil may be used to freshen breath. Orange oil has also been used in teeth whitening formulations. Preferably, the orange oil is organic orange oil.

Lemon oil is also an essential oil produced from the rind of lemon fruits. It is composed of mostly (greater than 90%) d-limonene, and is often used in place of pure d-limonene. The oil of the lemon's peel also has various uses. It is used as a wood cleaner and polish, where its solvent property is employed to dissolve old wax, fingerprints, and grime. Lemon oil and orange oil are also used as a nontoxic insecticide treatment. Lemon oil has also been shown to display useful antimicrobial properties. Lemon oil has been used for its bleaching properties that can help whiten teeths, and it has been used in mouthwashes. Preferably, the lemon oil is organic lemon oil.

Coconut oil is an edible oil extracted from the kernel or meat of matured coconuts harvested from the coconut palm (*Cocos nucifera*). It has various applications in food, medicine, and industry. Because of its high saturated fat content it is slow to oxidize and, thus, resistant to rancidification, lasting up to two years without spoiling. Coconut oil can be used as a skin moisturizer, helping with dry skin and reduces protein loss when used in hair. Before the advent of electrical lighting, coconut oil was the primary oil used for illumination in India and was exported as cochin oil. Coconut oil has also been used as a teeth whitener, and has been shown to have antiseptic, antibacterial and anti-inflammatory properties. Preferably, the coconut oil is virgin coconut oil. Most preferably, the coconut oil is organic virgin coconut oil.

Borage oil is obtained from Borage (*Borago officinalis*), also known as a starflower, is an annual herb. It is native to the Mediterranean region and has naturalized in many other locales. It grows satisfactorily in gardens in the UK climate, remaining in the garden from year to year by self-seeding. The leaves are edible and the plant is grown in gardens for that purpose in some parts of Europe. The plant is also commercially cultivated for borage seed oil extracted from its seeds. Preferably, the borage oil is organic borage oil.

Borage seed oil has one of the highest amounts of γ-linolenic acid (GLA) of seed oils—higher than blackcurrant seed oil or evening primrose oil, to which it is considered similar. GLA comprises around 24% of the oil typically. GLA is converted to dihomo-gamma-linolenic acid, a precursor to a variety of the 1-series prostaglandins and the 3-series leukotrienes. It inhibits leukotriene synthesis to provide therapy in rheumatologic illness. Borage seed oil may therefore have anti-inflammatory and anti-thrombotic effects and it has been studied for its potential to treat anti-inflammatory disorders, arthritis, atopic eczema, and respiratory inflammation. Borage seed oil supplements have been shown to reduce gum inflammation (gingivitis) and improve gum health in people with inflammation in the areas of the mouth around the teeth (periodontitis). Borage oil is also considered an alkaline food as it has a moderately alkalizing effect on the body.

Borage oil may contain the pyrrolizidine alkaloid amabiline, which is hepatotoxic leading to a risk of liver damage. Patients should use borage oil certified free of unsaturated pyrrolizidine alkaloids. Borage oil may be unsafe during pregnancy because preliminary studies suggest borage oil has a teratogenic effect and that its prostaglandin E agonist action may cause premature labor. Seizures have been reported as a complication of ingestion of borage oil in doses of 1,500 to 3,000 mg daily, although a mixed review of borage oil's effect on seizure thresholds indicates that borage oil quality varies. A specific extraction process may offer purified products with 50%+ GLA content.

Pumpkin seed oil is obtained by pressing pumpkin seeds. Pumpkin seed oil has a high content of omega-3, -6 and -9 fatty acids, which makes it a highly nutritious and valuable oil.

Flora Pumpkin Seed Oil contains: 43% polyunsaturated Linoleic acid (omega-6), 36% monounsaturated Oleic acid (omega-9), 14% polyunsaturated Alpha-linolenic acid (omega-3), 8% saturated fatty acids. It also contains vitamins, including vitamins A, B1, B2, B3, B5, B6, B12, C, E, and minerals such as zinc, calcium, copper, iodine, iron, magnesium, manganese, phosphorus, potassium, selenium; folate, tryptophan, lysine and phytosteroles. It has been associated with the prevention of bladder, kidney, urinary tract and prostate conditions. It has been shown to have antioxidant activity.

According to an embodiment, the oil may be present from about 2% to about 50% (vol/vol) of the composition. Preferably, the orange oil may be from about 6% to about 15% (vol/vol) of the composition. The lemon oil may preferably be from about 10% to about 20% (vol/vol) of the composition. The coconut oil may preferably be from about 2% to about 10% (vol/vol) of the composition. The coconut oil is preferably liquid coconut oil. The borage oil may preferably be from about 2% to about 5% (vol/vol) of the composition.

Tinctures

According to an embodiment, the personal care composition of the present invention may contain at least one tincture chosen from dulse seaweed extract tincture or papaya leaf extract tincture.

A tincture is typically an alcoholic extract of plant or animal material or solution of such or of a low volatility substance (such as iodine and mercurochrome). To qualify as an alcoholic tincture, the extract should have an ethanol percentage of at least 40-60% or 80-120 proof. Sometimes even a 90% or 180 proof tincture is achieved. In herbal medicine, alcoholic tinctures are made with various concentrations of ethanol, 25% being the most common. Other concentrations include 45% and 90%. Herbal tinctures are not always made using ethanol as the solvent, though this is most commonly the case. Other solvents include vinegar, glycerol, ether and propylene glycol, not all of which can be used for internal consumption. Ethanol has the advantage of being an excellent solvent for both acidic and basic (alkaline) constituents.

Dulse seaweed extract tincture. *Palmaria palmata* (Linnaeus) Kuntze, also called dulse, dillisk or dilsk, red dulse, sea lettuce flakes or creathnach, is a red alga (Rhodophyta) previously referred to as *Rhodymenia palmata* (Linnaeus) Greville. It grows on the northern coasts of the Atlantic and Pacific oceans. It is a well-known snack food. Dulse is a good source of minerals and vitamins compared with other vegetables, and contains all trace elements needed by humans, and has a high protein content. It is capable of providing more than 100% of the daily required amount of vitamin B6, 66% of vitamin B12, 100% of the daily supply of iron and fluoride. It is relatively low on sodium and high in potassium. Extracts of dulse seaweed have been shown to have antioxidants and cell proliferation inhibitory properties in vitro.

Papaya leaves extract tincture. Papaya leaves contain beta-carotene, calcium, carpaine, fats, flavonols, niacin, papain, tannins, and vitamin C (in higher concentration in the leaf than in the fruit). The leaf, unlike the fruit, is not a source of the protein-dissolving enzyme papain, but the latex (sap) in the leaf stem is. Papain remains in leaf preparations that have been dried over low heat, but it may be destroyed in products that are dried at high heat. Papaya leaves and their extracts are also marketed as dietary supplements to enhance the immune system, to improve platelet function, and to prevent chemotherapy-related adverse effects. Papaya leaves exhibit anti-tumor, immunomodulatory, and antioxidant effects in vitro. The leaf extracts contain antibacterial compounds that inhibit the growth of a wide variety of Gram-positive and Gram-negative bacteria.

According to an embodiment, the tincture may be present in about 3% to about 20% (vol/vol) of the composition. According to an embodiment, the dulse seaweed extract tincture may preferably be present in about 3% to about 12% (vol/vol) of the composition. According to another embodiment, the papaya leaf extract tincture may be preferable present in about 5% to about 10% (vol/vol) of the composition. According to an embodiment, the tinctures used in the present invention may have concentrations of about 50 mg extract per quarter teaspoon (1.25 ml).

Edible Abrasives

According to an embodiment, the personal care composition of the present invention may contain at least one abrasive. Preferably, the abrasive is chosen from colloidal calcium or colloidal silica. Other suitable abrasives include but are not limited to aluminum hydroxide ($Al(OH)_3$), calcium carbonate ($CaCO_3$), various calcium hydrogen phosphates, various hydrated silicas ($SiO_2$ plus $H_2O$) and zeolites, diatomaceous earth, and hydroxyapatite ($Ca_5(PO_4)_3OH$). Abrasive are insoluble particles that help remove tartar (plaque) from the teeth, and help remove dead cells from the skin. In toothpaste systems, the abrasive silica was shown to be the principal tooth cleaning and abrasive agent.

According to an embodiment abrasives may constitute from about 0.100% to about 0.325% (wt/vol) of the composition of the present invention. According to an embodiment, the colloidal calcium may be from about 0.100% to about 0.275% (wt/vol) of the composition. According to another embodiment, the colloidal silica may be from about 0.02% to about 0.08% (wt/vol) of the composition.

Thickening Agents

According to an embodiment, the personal care composition of the present invention may contain at least one thickening agent chosen from carageenan, aloe vera gel, aloe vera juice, xanthan gum and cellulose gum.

Thickening agents, or thickeners, are substances which increase the viscosity of a solution or liquid/solid mixture without substantially modifying its other properties; although most frequently applied to foods where the target property is taste, the term also is applicable to paints, inks, explosives, etc. Thickeners may also improve the suspension of other ingredients or emulsions which increases the stability of the product. Thickening agents are often regulated as food additives and as cosmetics and personal hygiene product ingredients. Some thickening agents are gelling agents (gellants), forming a gel, dissolving in the liquid phase as a colloid mixture that forms a weakly cohesive internal structure. Examples of other suitable thickeners include but are not limited to alginic acid, sodium alginate, potassium alginate, ammonium alginate, calcium alginate, agar, locust bean gum, konjac gum, tara gum, acacia gum, guar gum a starch, pectin, carboxymethyl cellulose, a hydroxypropyl cellulose, a methyl cellulose and gelatin.

Aloe vera gel and juice. Aloe vera gel and juice have been used to treat common oral and dermal health conditions, including cold sores and fever blisters (outside of the mouth) and canker sores (in the mouth). Aloe vera gel and juice accelerates healing and reduces pain associated with external cold sores. In addition to their anti-viral and anti-inflammatory properties, aloe vera gel and juice provide benefits to the skin by adding amino acids and B1, B2, B6 and C vitamins. To treat a cold sore, apply aloe vera gel three until a lesion has dried.

Aloe vera juice also can help internal ulcerations of the mouth, including canker sores (a common condition usually caused by stress) and lichen planus (a disease of unknown origin affecting the skin and mucus membranes).

Xanthan gum is used as a thickening and stabilizing agent in foods, toothpastes, and medicines. Xanthan gum is also an ingredient in some sustained-release pills.

Cellulose gum is the common name for carboxymethylcellulose, or CMC. Its emulsifying properties make it especially useful for products with ingredients that tend to separate, such as yogurt and jellies. Its ability to bind water makes it especially useful for diet foods, which tend to substitute water or other liquids for fat. Cellulose gum also improves texture, so it is a common ingredient in ice cream and frosting, products in which smoothness is a mark of quality. Beer manufacturers also use cellulose gum to stabilize beer foam. These same properties are useful for some pharmaceutical products that tend to separate over time, such as toothpaste. In the cosmetics industry, cellulose gum appears in bath products, makeup, shaving gels and hair products.

According to another embodiment, the thickening agent may be present in the formulation in about 3% to about 66% (vol/vol). According to an embodiment, the aloe vera gel may be from about 5% to about 15% (vol/vol) of the composition. According to an embodiment, the cellulose gum may be from about 3% to about 10% of the composition. According to an embodiment, the xanthan gum may be from about 15% to about 20% of the composition. According to an embodiment, the aloe vera juice, may be from about 6% to about 10% of the composition.

According to another embodiment, the carrageenan may be from about 0.1% to about 0.3% (wt/vol) of the composition. According to another embodiment, the carrageenan may be from about 0.2% to about 0.25% (wt/vol) of the composition. According to another embodiment, the carrageenan may be about 0.23% of the composition.

Humectants

According to another embodiment, the composition of the present invention may further comprise a humectant. Humectants are substance used to keep things moist. When used as a food additive, the humectant has the effect of keeping the foodstuff moist. Humectants are also found in many cosmetic products where moisturization is desired, including treatments such as moisturizing hair conditioners and also commonly used in body lotions. Examples of humectants include but are not limited to propylene glycol, as well as hexylene glycol and butylene glycol, glyceryl triacetate, vinyl alcohol, neoagarobiose, sugar polyols such as glycerol, sorbitol, xylitol and maltitol, polymeric polyols like polydextrose, quillaia, lactic acid, urea, glycerin, aloe vera gel, MP Diol, alpha hydroxy acids like sodium lactate, lactic acid, tartaric acid, malic acid, glycolic acid, glucose, citric acid, and combinations thereof, and honey. According to another embodiment, the preferred humectant may glycerin.

According to another embodiment of the present invention, the humectant may be from about 2% to about 5% (vol/vol) of the composition.

Emulsifier

According to an embodiment, the composition of the present invention may further comprise an emulsifier. An emulsifier is a substance that stabilizes an emulsion by increasing its kinetic stability. According to an embodiment, the emulsifier may be a lecithin, a vegetal pulp powder (such as citrus pulp powder, baobab pulp powder, mango pulp powder, tomato pulp powder, pumpkin pulp powder, guava pulp powder, papaya pulp powder and beet pulp powder), and citric acid. The preferred emulsifier is citric acid.

According to another embodiment of the present invention, the emulsifier may be from about 4% to about 10% (wt/vol) of the composition.

The present invention will be more readily understood by referring to the following examples which are given to illustrate the invention rather than to limit its scope.

Example 1

| ANTI-AGING FORMULA 72 | | |
| --- | --- | --- |
| Ingredients | % (vol/vol) | Cumulative % |
| Food Grade Orange Oil | 12 | 12 |
| Liquid Coconut Oil | 5 | 17 |
| Dulse Seaweed Extract Tincture (50 mg/1.25 ml) | 12 | 29 |
| Food Grade Lemon Oil | 10 | 39 |
| Extra Strength Calcium in Water (35 mg/1.25 ml) | 4 | 43 |
| Papaya Leaf Extract Tincture (50 mg/1.25 ml) | 7 | 50 |
| Colloidal Silica (9 mg/5 ml) | 30 | 80 |
| *Aloe Vera* Gel | 15 | 95 |
| Cellulose Gum | 5 | 100 |
| S/T | 100 | |

This liquid formulation may be used as an anti-aging formulation as well as a detoxifier.

Example 2

| MAKE-UP REMOVER FORMULA 75 | | |
| --- | --- | --- |
| Ingredients | % (vol/vol) | Cumulative % |
| Food Grade Orange Oil | 8 | 8 |
| Liquid Coconut Oil | 2 | 10 |
| Dulse Seaweed Extract Tincture (50 mg/1.25 ml) | 12 | 22 |

-continued

| MAKE-UP REMOVER FORMULA 75 | | |
| --- | --- | --- |
| Ingredients | % (vol/vol) | Cumulative % |
| Food Grade Lemon Oil | 12 | 34 |
| *Borage* Oil | 4 | 38 |
| Extra Strength Calcium in Water (35 mg/1.25 ml) | 7 | 45 |
| Papaya Leaf Extract Tincture (50 mg/1.25 ml) | 7 | 52 |
| Colloidal Silica (9 mg/5 ml) | 7 | 59 |
| *Aloe Vera* Gel | 5 | 64 |
| Xanthan Gum | 20 | 84 |
| Vegetable Glycerin | 4 | 88 |
| Cellulose Gum | 8 | 96 |
| Citric Acid | 4 | 100 |
| S/T | 100 | |

This formulation is a good make-up remover, exfoliant, and works well as a general skin healing product that helps healing of burns, sunburns, and eczema.

Example 3

| TARTAR REMOVAL FORMULA #1 | | |
| --- | --- | --- |
| Ingredients | % (vol/vol) | Cumulative % |
| Active Ingredients | | |
| Food Grade Orange Oil | 10.0 | 10.0 |
| Liquid Coconut Oil | 9.0 | 19.0 |
| Dulse Seaweed Extract Tincture (50 mg/1.25 ml) | 3.0 | 22.0 |
| Food Grade Lemon Oil | 20.0 | 42.0 |
| *Borage* Oil | 5.0 | 47.0 |
| Extra Strength Calcium in Water (35 mg/1.25 ml) | 9.0 | 56.0 |
| Papaya Leaf Extract Tincture (50 mg/1.25 ml) | 8.0 | 64.0 |
| Colloidal Silica (9 mg/5 ml) | 5.0 | 69.0 |
| *Aloe Vera* Gel | 8.0 | 77.0 |
| Carrageenan (1% wt/vol) | 23.0 | 100.0 |
| Total | 100.0 | |

This formulation may be used for tartar removal by application to the teeth with a brush or other suitable means. Repeated application of the formulation over time weakens tartar buildups, and eventually dissolves them. The formulation is intended for use as a fluoride-free cleanser for teeth. The formula is fluoride free and uses food grade ingredients.

Example 4

| TARTAR REMOVAL FORMULATION #2 | | |
| --- | --- | --- |
| Ingredients | % (vol/vol) | Cumulative % |
| Food Grade Orange Oil | 6 | 6 |
| Liquid Coconut Oil | 3 | 9 |
| Dulse Seaweed Extract Tincture (50 mg/1.25 ml) | 12 | 21 |
| Food Grade Lemon Oil | 11 | 32 |
| *Borage* Oil | 2 | 34 |
| Extra Strength Calcium in Water (35 mg/1.25 ml) | 6 | 40 |
| Papaya Leaf Extract Tincture (50 mg/1.25 ml) | 6 | 46 |

| TARTAR REMOVAL FORMULATION #2 | | |
| --- | --- | --- |
| Ingredients | % (vol/vol) | Cumulative % |
| Colloidal Silica (9 mg/5 ml) | 13 | 59 |
| *Aloe Vera* Juice | 6 | 65 |
| Xanthan Gum | 20 | 85 |
| Cellulose Gum | 3 | 88 |
| Vegetable Glycerin | 3 | 91 |
| Citric Acid | 9 | 100 |
| S/T | 100 | |

This formulation may be used for tartar removal by application to the teeth with a brush or other suitable means. Repeated application of the formulation over time weakens tartar buildups, and eventually dissolves them. The formulation is intended for use as a fluoride-free cleanser for teeth. The formula is fluoride free and uses food grade ingredients.

Example 5

| TARTAR REMOVAL FORMULATION #3 | | |
| --- | --- | --- |
| Ingredients | % (vol/vol) | Cumulative % |
| Food Grade Orange Oil | 6 | 6 |
| Virgin Coconut Oil (Melted) | 10 | 16 |
| Dulse Seaweed Extract Tincture (50 mg/1.25 ml) | 14 | 30 |
| Food Grade Lemon Oil | 6 | 36 |
| *Borage* Oil | 3 | 39 |
| Extra Strength Calcium in Water | 5 | 44 |
| Papaya Leaf Extract Tincture (50 mg/1.25 ml) | 20 | 64 |
| Colloidal Silica (9 mg/5 ml) | 10 | 74 |
| *Aloe Vera* Gel | 15 | 89 |
| Xanthan Gum | 2 | 91 |
| Cellulose Gum | 9 | 100 |
| S/T | 100 | |

This formulation may be used for tartar removal by application to the teeth with a brush or other suitable means. Repeated application of the formulation over time weakens tartar buildups, and eventually dissolves them. The formulation is intended for use as a fluoride-free cleanser for teeth. The formula is fluoride free and uses food grade ingredients.

For preparation of the formulation, all the liquid ingredients are mixed together at a temperature slightly above room temperature (25-30° C.). The xanthan gum is added to the mixed ingredients and mixed on low speed until the composition is homogeneous. The cellulose gum is added to the mixed ingredient and mixed on low speed until the composition is homogeneous.

Example 6

| TARTAR REMOVAL FORMULATION #81 | | |
| --- | --- | --- |
| Ingredients | % Volume | Cumulative % |
| Food Grade Orange Oil | 6 | 6 |
| Virgin Coconut Oil (Melted) | 5 | 11 |
| Pumpkin Seed Oil | 5 | 16 |
| Dulse Seaweed Extract Tincture | 14 | 30 |
| Food Grade Lemon Oil | 6 | 36 |

TARTAR REMOVAL FORMULATION #81

| Ingredients | % Volume | Cumulative % |
| --- | --- | --- |
| *Borage* Oil | 3 | 39 |
| Extra Strength Calcium in Water | 5 | 44 |
| Papaya Leaf Extract Tincture | 20 | 64 |
| Colloidal Silica | 10 | 74 |
| *Aloe Vera* Gel | 15 | 89 |
| Xanthan Gum | 2 | 91 |
| Cellulose Gum | 9 | 100 |
| S/T | 100 | |

This formulation may be used for tartar removal by application to the teeth with a brush or other suitable means. Repeated application of the formulation over time weakens tartar buildups, and eventually dissolves them. The formulation is intended for use as a fluoride-free cleanser for teeth. The formula is fluoride free and uses food grade ingredients.

For preparation of the formulation, all the liquid ingredients are mixed together at a temperature slightly above room temperature (25-30° C.). The xanthan gum is added to the mixed ingredients and mixed on low speed until the composition is homogeneous. The cellulose gum is added to the mixed ingredient and mixed on low speed until the composition is homogeneous.

Example 7

TOOTH PASTE FORMULATION

| Ingredients | % (vol/vol) | Cumulative % |
| --- | --- | --- |
| Food Grade Orange Oil | 6.0 | |
| Liquid Coconut Oil | 3.0 | 9.0 |
| Dulse Seaweed Extract Tincture (50 mg/1.25 ml) | 12.0 | 21.0 |
| Food Grade Lemon Oil | 11.0 | 32.0 |
| *Borage* Oil | 2.0 | 34.0 |
| Extra Strength Calcium in Water (35 mg/1.25 ml) | 6.0 | 40.0 |
| Papaya Leaf Extract Tincture (50 mg/1.25 ml) | 6.0 | 46.0 |
| Colloidal Silica (9 mg/5 ml) | 13.0 | 59.0 |
| *Aloe Vera* Gel | 6.0 | 65.0 |
| Xanthan Gum | 20.0 | 85.0 |
| Cellulose Gum | 3.0 | 88.0 |
| Vegetal Glycerin | 3.0 | 91.0 |
| Citric Acid | 9% | 100 |
| Total | | 100% |

The toothpaste formulation has a fresh citrus taste, and is capable of remove stains from the teeth.

Example 8

Use of the Tartar Removal Formulation for Oral Hygiene

Four subject having histories of teeth and gum sensitivities were provided with the tartar removal formulation of example 6 for use as a regular daily use as a dental cleaning composition.

Subject 1, female, used the tartar removal formulation for two weeks before a dentist appointment. The dental hygienist observed that the gums appeared to be healthier than they had been for the past few years. The dental office had been monitoring the subject's gums for possible gum disease and noticed a marked improvement. In addition, the subject noticed that her teeth were much less sensitive to the scaling procedure. The dental hygienist also noticed that some problems areas in the mouth, because of the teeth being so close together, were much improved with less tartar buildup.

The subject discontinued use of the toothgel until about five days before her next dentist appointment six months later. Nevertheless, the hygienist was surprised that the subject's gums were so healthy looking. Again, there was very little sensitivity when scaling procedure took place and problem areas that were usually problematic remained improved.

Subject 2, female, used the tartar removal formulation two a day, for five days, before a dentist appointment. The subject observed much less sensitivity during the scaling procedure. Also, the dental hygienist observed that the subject 2 had been performing a better job of cleaning her teeth, as there was less tartar buildup and the subject's gum appeared healthier.

Subject 3, female, used the tartar removal formulation on and off for a year. She noticed that her teeth were not as sensitive to cold as they use to be, her teeth felt stronger, her gums were less sensitive and felt healthier, and her mouth felt good in the morning, even before brushing.

On a first visit to the dentist after using the tartar removal formulation for two weeks, the dental hygienist remarked that subject 3's teeth did not need much scaling. The dentist performed the periodontal disease examination for deep pockets in subject's gums. The result was that there were no pockets more than "2" on a scale of 0 to 3, where "0" is the worse (unhealthy), and "3" is considered healthy.

For about 1½ months, subject 3 used her regular toothpaste that she had been using before for sensitive teeth. She noticed that her teeth were more sensitive to cold than they were using the tartar removal formulation. She also developed a spot on my lower left gum line that was sore and but was not getting better with regular brushing. Once she received another sample of tartar removal formulation, her gums healed within two days. She also used the tartar removal formulation for two weeks before going back to the dentist again. Also, Since using the tartar removal formulation, subject 3 went back to the dentist twice, for 3 appointments in total. She has had no cavities, no gum recession, and in every instance much less scaling than usual. Importantly subject 3 enjoyed a much more relaxed experience at the dentist because there was no pain during the teeth cleaning procedure.

Subject 4, female, used the tartar removal formulation for normal dental hygiene. Subject 4 notices that her teeth felt clean, and her mouth felt clean even after getting up in the morning. Visits to the dentist revealed that she had a reduced amount of tartar buildup, as less scaling was necessary during the cleaning procedure.

Being prone to canker sores (aphthous stomatitis), subject 4 also applied a small quantity of the tartar removal formulation. Within 3 daily applications, the canker sore had significantly healed, and was gone within a few days.

Example 10

Use of the Tartar Removal Formulation for Skin Treatment

Subject 5, female, commonly develops rashes and cracked lips which takes several days, even weeks to heal. She has tried a number of lip balms on her lesions, and medicated lip balm and non-medicated lip balms have the same result: neither one really helps the heal process. Subject 5 used the tartar removal formulation of example 6 on her lips. Subject 5 observed some healing overnight, as the lesions looked more like normal lip skin, and the pain was reduced almost immediately. She observed that her lips were healed completely in 3 days.

Example 11

Use of the Makeup Removal Formulation

Subject 6, female used the makeup removal formulation of example 2. The makeup removal formulation has been used on sunburns on a number of occasions, and took the pain away immediately, while the skin did not peel afterwards. The makeup removal formulation has also been used on skin rashes, and pimples and it took itchiness away and healed up overnight. Lastly, Subject 6 found that the makeup removal formulation also works well as an exfoliant. Even though the formula is mostly oils, it is does not feel greasy on the skin. Her skin feels very soft and smooth after using it.

Subject 7, female also used the makeup removal formulation of example 2 on sunburns on a number of occasions, and commented that it took the pain away immediately, while the skin did not peel afterwards. The makeup removal formulation has also been used on skin rashes, and pimples and it took itchiness away and healed up overnight. Lastly, Subject 7 found that the makeup removal formulation also works well as an exfoliant.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A surfactant free personal care emulsion comprising:
   at least one edible oil selected from the group consisting of:
      orange oil from about 5% to about 15% (vol/vol) of the emulsion,
      coconut oil from about 2% to about 10% (vol/vol) of the emulsion,
      lemon oil from about 6% to about 20% (vol/vol) of the emulsion, and combinations thereof;
   at least one edible abrasive selected form the group consisting of:
      colloidal calcium from about 0.02% to about 0.325% (wt/vol) of the emulsion,
      colloidal silica from about 0.02% to about 0.325% (wt/vol) of the emulsion, and a combination thereof;
   a thickening agent mixture consisting:
      at least one thickening agent chosen from aloe vera gel from about 5% to about 15% (vol/vol) of the emulsion, aloe vera juice from about 6% to about 10% (vol/vol) of the emulsion, xanthan gum from about 2% to about 20% (vol/vol) of the emulsion, and cellulose gum from about 3% to about 9% (vol/vol) of the emulsion,
      carrageenan from about 0.1% to about 0.3% (wt/vol) of the emulsion, or combinations thereof;
   at least one tincture selected from the group consisting of:
      dulse seaweed extract tincture from about 3% to about 14% (vol/vol) of the emulsion,
      papaya leaf extract tincture from about 6% to about 20% (vol/vol) of the emulsion, and a combination thereof; and
   a humectant comprising:
      glycerin from about 2% to about 5% (vol/vol) of the emulsion.

2. The surfactant free personal care emulsion of claim 1, wherein said orange oil is from about 6% to about 12% (vol/vol) of the emulsion.

3. The surfactant free personal care emulsion of claim 1, wherein said at least one edible abrasive is from about 0.1% to about 0.325% (wt/vol) of the emulsion.

4. The surfactant free personal care emulsion of claim 1, wherein said humectant further comprises propylene glycol, hexylene glycol, butylene glycol, a vinyl alcohol, glyceryl triacetate, neoagarobiose, a sugar polyol, a polymeric polyol, quillaia, lactic acid, urea, 2-Methyl-1,3-propanediol (MP diol), honey, and combinations thereof.

5. The surfactant free personal care emulsion of claim 4, wherein said sugar polyol is one or more of sorbitol, xylitol and maltitol.

6. The surfactant free personal care emulsion of claim 1, wherein said glycerin is from about 3% to about 4% (vol/vol) of the emulsion.

7. The surfactant free personal care emulsion of claim 1, wherein said emulsion is fluoride free.

8. A surfactant free personal care emulsion consisting of:
   at least one edible oil selected from the group consisting of:
      orange oil from about 5% to about 15% (vol/vol) of the emulsion,
      coconut oil from about 2% to about 10% (vol/vol) of the emulsion,
      lemon oil from about 6% to about 20% (vol/vol) of the emulsion, and combinations thereof;
   at least one edible abrasive selected form the group consisting of:
      colloidal calcium from about 0.02% to about 0.325% (wt/vol) of the emulsion,
      colloidal silica from about 0.02% to about 0.325% (wt/vol) of the emulsion, and a combination thereof;
   a thickening agent mixture consisting of:
      at least one thickening agent chosen from aloe vera gel from about 5% to about 15% (vol/vol) of the emulsion, aloe vera juice from about 6% (vol/vol) of the emulsion, xanthan gum from about 2% to about 20% (vol/vol) of the emulsion, and cellulose gum from about 3% to about 9% (vol/vol) of the emulsion,
      carrageenan from about 0.1% to about 0.3% (wt/vol) of the emulsion, or
      combinations thereof;
   at least one tincture selected from the group consisting of:
      dulse seaweed extract tincture from about 3% to about 14% (vol/vol) of the emulsion,
      papaya leaf extract tincture from about 6% to about 20% (vol/vol) of the emulsion, and
      a combination thereof; and
   a first humectant consisting of glycerin from about 2% to about 5% (vol/vol) of the emulsion, and optionally a second humectant selected from the group consisting of propylene glycol, hexylene glycol, butylene glycol, a vinyl alcohol, glyceryl triacetate, neoagarobiose, a sugar polyol, a polymeric polyol, quillaia, lactic acid, urea, 2-Methyl-1,3-propanediol (MP diol), honey, and combinations thereof.

9. The surfactant free personal care emulsion of claim 8, wherein said orange oil is from about 6% to about 12% (vol/vol) of the emulsion.

10. The surfactant free personal care emulsion of claim 8, wherein said at least one edible abrasive is from about 0.1% to about 0.325% (wt/vol) of the emulsion.

11. The surfactant free personal care emulsion of claim 8, wherein said sugar polyol is one or more of sorbitol, xylitol and maltitol.

12. The surfactant free personal care emulsion of claim 8, wherein said glycerin is from about 3% to about 4% (vol/vol) of the emulsion.

13. The surfactant free personal care emulsion of claim 8, wherein said emulsion is fluoride free.

* * * * *